US00PP16472P2

(12) United States Plant Patent
Kientzler

(10) Patent No.: US PP16,472 P2
(45) Date of Patent: Apr. 25, 2006

(54) **NEW GUINEA *IMPATIENS* PLANT NAMED 'VISINFDKP'**

(50) Latin Name: *Impatiens hawkeri*
Varietal Denomination: Visinfdkp

(75) Inventor: Ludwig Kientzler, Valverde Alajuela (CR)

(73) Assignee: Visio Plant, Valverde Vega Alajuela (CR)

( * ) Notice: Subject to any disclaimer, the term of this patent is extended or adjusted under 35 U.S.C. 154(b) by 185 days.

(21) Appl. No.: 10/937,848

(22) Filed: Sep. 9, 2004

(51) Int. Cl.
*A01H 5/00* (2006.01)

(52) U.S. Cl. ..... Plt./318
(58) Field of Classification Search ..... Plt./318
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of New Guinea *Impatiens* plant named 'Visinfdkp', characterized by its rounded and upright plant form; vigorous and freely branching growth habit; bushy appearance; dark green-colored foliage; freely flowering habit with flowers held above and beyond the foliage; and large dark pink-colored flowers.

1 Drawing Sheet

Botanical classification/cultivar designation: *Impatiens hawkeri* cultivar Visinfdkp.

BACKGROUND OF THE INVENTION

The present Invention relates to a new and distinct cultivar of New Guinea *Impatiens* plant, botanically known as *Impatiens hawkeri*, and hereinafter referred to by the cultivar name Visinfdkp.

The new *Impatiens* is a product of a planned breeding program conducted by the Inventor in Gensingen, Germany. The objective of the breeding program is to develop new vigorous New Guinea *Impatiens* cultivars with large flowers and interesting and unique flower and foliage colors.

The new *Impatiens* originated from a cross-pollination made by the Inventor in September, 2001, of a proprietary *Impatiens hawkeri* selection identified as code number 01-222, not patented, as the female, or seed parent, with a proprietary *Impatiens hawkeri* selection identified as 01-598, not patented, as the male, or pollen parent. The cultivar Visinfdkp was discovered and selected by the Inventor as a flowering plant within the progeny of the stated cross-pollination in a controlled environment in Gensingen, Germany in March, 2002.

Asexual reproduction of the new cultivar by terminal cuttings at Gensingen, Germany, since March, 2002, has shown that the unique features of this new *Impatiens* are stable and reproduced true to type in successive generations.

SUMMARY OF THE INVENTION

The following traits have been repeatedly observed and are determined to be the unique characteristics of 'Visinfdkp'. These characteristics in combination distinguish 'Visinfdkp' as a new and distinct *Impatiens* cultivar:

1. Rounded and upright plant form.
2. Vigorous and freely branching growth habit; bushy appearance.
3. Dark green-colored foliage.
4. Freely flowering habit with flowers held above and beyond the foliage.
5. Large dark pink-colored flowers.

Plants of the new *Impatiens* differ from plants of the female parent selection in the following characteristics:

1. Plants of the new *Impatiens* have larger flowers than plants of the female parent selection.
2. Plants of the new *Impatiens* are more freely flowering than plants of the female parent selection.

Plants of the new *Impatiens* differ from plants of the male parent selection in the following characteristics:

1. Plants of the new *Impatiens* are more vigorous than plants of the male parent selection.
2. Plants of the new *Impatiens* are more uniform than plants of the male parent selection.

Plants of the new *Impatiens* can be compared to plants of the cultivar Bonaire, disclosed in U.S. Plant Pat. No. 9,137. In side-by-side comparisons conducted in Gensingen, Germany, plants of the new *Impatiens* differed from plants of the cultivar Bonaire in the following characteristics:

1. Plants of the new *Impatiens* were more vigorous than plants of the cultivar Bonaire.
2. Plants of the new *Impatiens* had larger flowers than plants of the cultivar Bonaire.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Impatiens*.

The photograph at the top of the sheet comprises a side perspective view of a typical flowering plant of 'Visinfdkp' grown in a container.

The photograph at the bottom of the sheet comprises a close-up view of typical flowers and leaves of 'Visinfdkp'.

DETAILED BOTANICAL DESCRIPTION

The cultivar Visinfdkp has not been observed under all possible environmental conditions. The phenotype may vary somewhat with variations in environment such as temperature and light intensity, without, however, any variance in genotype. The aforementioned photographs and the following observations and measurements describe plants grown in Bonsall, Calif., during the summer under commercial practice in a polypropylene-covered shadehouse providing 50% light reduction with day temperatures ranging from 21 to 35° C. and night temperatures ranging from 18 to 24° C. Plants used in the photographs and following description were about ten weeks old and grown in 15.25-cm containers with one plant per container.

In the following description, color references are made to The Royal Horticultural Society Colour Chart, 1955 Edition, except where general terms of ordinary dictionary significance are used.

Botanical classification: *Impatiens hawkeri* cultivar Visinfdkp.

Parentage:

*Female, or seed, parent.*—Proprietary *Impatiens hawkeri* selection identified as code number 01-222, not patented.

*Male, or pollen, parent.*—Proprietary *Impatiens hawkeri* selection identified as code number 01-598, not patented.

Propagation:

*Type cutting.*—Terminal cuttings.

*Time to initiate roots, summer.*—About 10 days at 18° C.

*Time to initiate roots, winter.*—About 14 days at 18° C.

*Time to produce a rooted cutting or liner, summer.*—About 14 days at 18° C.

*Time to produce a rooted cutting or liner, winter.*—About 18 days at 18° C.

*Root description.*—Fine and freely branching; white in color.

Plant description:

*General appearance.*—Rounded and upright; vigorous growth habit.

*Growth and branching habit.*—Freely branching with about nine or ten lateral branches developing at the base, dense and bushy growth. Pinching, that is, removal of the terminal apices, is typically not required.

*Plant height.*—About 21 cm.

*Plant diameter.*—About 33 cm.

*Lateral branches.*—Length: About 16 cm. Diameter: About 1 cm. Internode length: About 3.4 cm. Texture: Smooth, glabrous. Color: 59A.

*Foliage description.*—Arrangement: Opposite or in whorls; simple. Length: About 9.2 cm. Width: About 4.4 cm. Shape: Elliptic. Apex: Acuminate. Base: Attenuate. Margin: Serrulate with ciliation. Texture, upper and lower surfaces: Smooth, glabrous. Color: Developing foliage, upper surface: 147A. Developing foliage, lower surface: 183B. Fully expanded foliage, upper surface: Darker than 147A. Fully expanded foliage, lower surface: 183B. Venation, upper surface: 185B. Venation, lower surface: 183A. Petiole: Length: About 2.3 cm. Diameter: About 3 mm. Texture, upper and lower surfaces: Smooth, glabrous. Color, upper and lower surfaces: 185A to 185B.

Flower description:

*Flower type and flowering habit.*—Single axillary flowers. Freely flowering, usually about eight flowers and flower buds per lateral branch. Flowers positioned above and beyond the foliage and typically face upward or outward. Flowers mostly flat; roughly rounded in shape. Flowers last about seven days on the plant. Petals self-cleaning; gynoecium persistent. Flowers not fragrant.

*Flowering season.*—Year-round under greenhouse conditions. In the garden, flowering from spring until fall.

*Flower height.*—About 5.5 cm.

*Flower width.*—About 5.8 cm.

*Flower depth.*—About 3 cm.

*Flower buds (at stage of showing color).*—Length: About 2.1 cm. Diameter: About 1.1 cm. Shape: Ovoid. Color: 67B.

*Petals.*—Quantity: Single, five per flower. Length: Banner petal: About 2.8 cm. Lateral petals: About 3 cm. Base petals: About 3.6 cm. Width: Banner petal: About 4.6 cm. Lateral petals: About 3.5 cm. Base petals: About 4 cm. Shape: Cordate. Apex: Emarginate. Base: Acute. Margin: Entire. Texture, upper and lower surfaces: Smooth; velvety. Color: When opening, upper surface: 67A. When opening, lower surface: 67C. Fully opened, upper surface: 67A; towards the base, 57A to 60A. Fully opened, lower surface: 67B.

*Spur.*—Length: About 4 cm. Diameter, at flower base: About 3 mm. Diameter, at apex: Less than 1 mm. Texture: Smooth, glabrous. Color: 59B.

*Peduncles.*—Length: About 4.2 cm. Diameter: About 2 mm. Strength: Strong. Angle: About 45° from vertical. Texture: Smooth, glabrous. Color: Darker than 185A.

*Reproductive organs.*—Androecium: Stamen number: Five fused at anthers, filaments free. Anther shape: Obovate. Anther size: About 3 mm by 6 mm. Anther color: 155A. Amount of pollen: Moderate. Pollen color: 158B. Gynoecium: Pistil length: About 4 mm. Stigma shape: Rounded. Stigma color: 67D. Style color: 144B. Ovary color: 144B.

*Seed/fruit.*—Seed and fruit development has not been observed.

Disease/pest resistance: Plants of the new *Impatiens* have not been observed to be resistant to pathogens and pests common to *Impatiens*.

Temperature tolerance: Plants of the new *Impatiens* have been observed to tolerate temperatures from 5 to 35° C.

It is claimed:

1. A new and distinct cultivar of New Guinea *Impatiens* plant named 'Visinfdkp', as illustrated and described.

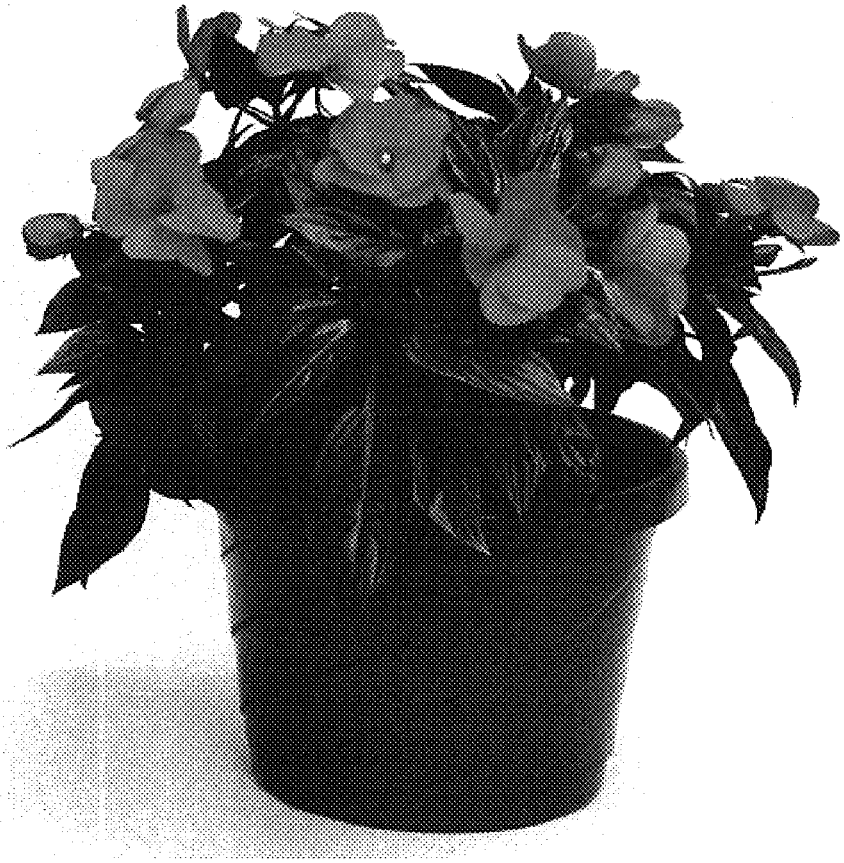
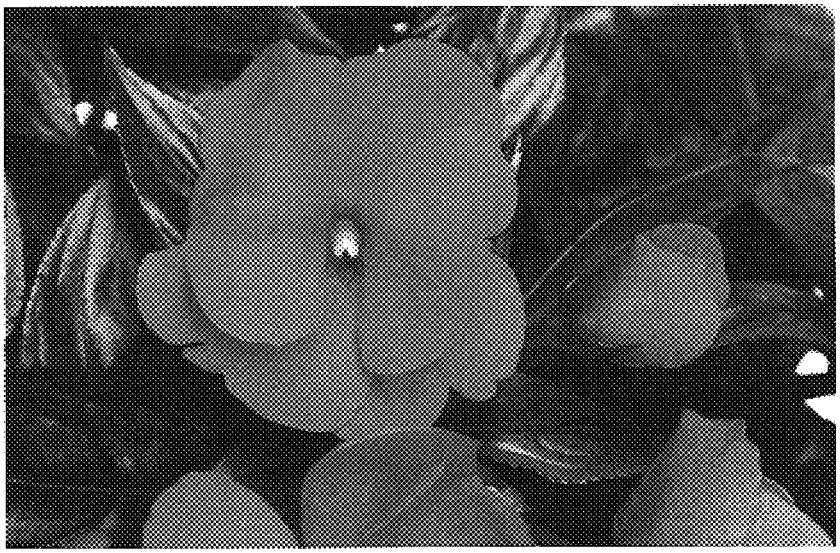

* * * * *